United States Patent [19]
DeCarlo, Jr. et al.

[11] Patent Number: 5,725,591
[45] Date of Patent: Mar. 10, 1998

[54] ACETABULAR BEARING SYSTEM

[75] Inventors: Alfred F. DeCarlo, Jr., Stamford; George B. Cipolletti, Wilton, both of Conn.; Leda Hewka, New York, N.Y.

[73] Assignee: Johnson & Johnson Professional, Inc., Raynham, Mass.

[21] Appl. No.: 696,310

[22] Filed: Aug. 13, 1996

[51] Int. Cl.[6] .................................................. A61F 2/32
[52] U.S. Cl. .................................... 623/22; 606/99
[58] Field of Search ........................... 623/19, 22, 23; 606/99

[56] References Cited

U.S. PATENT DOCUMENTS

| | | | |
|---|---|---|---|
| 4,695,282 | 9/1987 | Forte et al. | 623/22 |
| 4,795,469 | 1/1989 | Oh | 623/22 |
| 4,908,033 | 3/1990 | Frey et al. | 623/22 |
| 4,919,674 | 4/1990 | Schelhas | 623/22 |
| 4,936,855 | 6/1990 | Sherman | 623/22 |
| 4,960,427 | 10/1990 | Noiles | 623/22 |
| 5,021,062 | 6/1991 | Adrey et al. | 623/22 |
| 5,282,864 | 2/1994 | Noiles et al. | 623/22 |
| 5,314,491 | 5/1994 | Thongpreda et al. | 623/22 |

*Primary Examiner*—David Isabella
*Assistant Examiner*—Tram Anh T. Nguyen
*Attorney, Agent, or Firm*—Susan M. Schmitt

[57] ABSTRACT

An acetabular cup system is provided in which an insert or liner may be selected from a plurality of types of inserts to be used with an acetabular shell. One insert may be oriented after it is removably inserted into the acetabular shell. After an orientation is selected, it may be permanently fixed by pins. The other insert includes a snap-in ring that allows the insert to be snapped into position with the shell after its orientation is selected. The snap-in insert and ring are removable from the shell using a device for removing such snap-in insert and ring.

7 Claims, 3 Drawing Sheets

5,725,591

1

ACETABULAR BEARING SYSTEM

FIELD OF THE INVENTION

The present invention relates to hip prosthetic implants and in particular to acetabular bearings that are insertable into and orientable with respect to a corresponding acetabular shell to optimally orient the bearing when implanting the shell and bearing into the acetabulum of a patient.

BACKGROUND OF THE INVENTION

A typical acetabular cup of a hip implant comprises an outer shell and an inner bearing rotatable within the outer shell about a common axis. The inner bearing preferably has an asymmetric lip extending from the shell and having an angular orientation that varies about the circumference of the liner. Such liners are used to orient the angle of the acetabular cup to provide the greatest range of hip motion while providing a means for preventing dislocation. Accordingly in a hip implant procedure, the liner is rotated within an acetabular shell until the most confining or closed angle is located approximately where the femoral head has a tendency to dislocate from the acetabular cup thereby minimizing the risk of dislocation.

Generally two types of cups are presently used. A first of these types includes a bearing that is insertable into the shell and rotatable within the shell to various positions from which the ideal or optimal angular orientation of the cup may be selected. Typically such a shell and liner consist of a groove within the shell for receiving lugs of the liner and a number of protrusions from the outer shell over the groove that holds the liner in place once the liner is rotated within the shell. Such liner is readily removable from the shell during an implant procedure until pins or plugs are used to lock the two components together.

The second type of orientable liner comprises a liner that may be rotated about the common axis before inserting into the shell. When the optimal position is identified the shell may be snapped into place and secured into position with a resilient ring placed around the insert. These types of liners are preferred by some surgeons while the first type is preferred by others. The second type of liner, however, is not easily removable from the shell without damaging the liner or shell so that the liner may not be used again within the shell.

Therefore, it is desirable to provide a system in which the surgeon may select the type of liner the surgeon wishes to use according to his or her preference. It is also desirable to provide a snap-in type liner which may be easily removed from the shell without damaging the liner, shell or other components of the acetabular cup.

SUMMARY OF THE INVENTION

Accordingly, the present invention provides an acetabular cup system including cup inserts or liners of each of the two types described above, i.e., the insert-then-orient type and the orient-then-insert or snap-in type, both of which may be used with the same acetabular shell.

One feature of the snap-in type acetabular insert of the present invention also provides a means for easily removing the insert from the acetabular shell without damaging the shell or liner.

This system comprises an orientable acetabular liner with an asymmetric lip that may be inserted into an acetabular shell and then rotated into a selected angular orientation and fixed in such position with pins. The system further comprises a snap-in liner and ring that may be used with the same acetabular shell wherein the liner orientation is first selected then the liner is snapped into a locked position within the shell.

These and other features of the invention are exemplified in the following Detailed Description of the Drawings and Detailed Description of the Invention.

DETAILED DESCRIPTION OF THE DRAWINGS

DETAILED DESCRIPTION OF THE INVENTION

Figure 1:
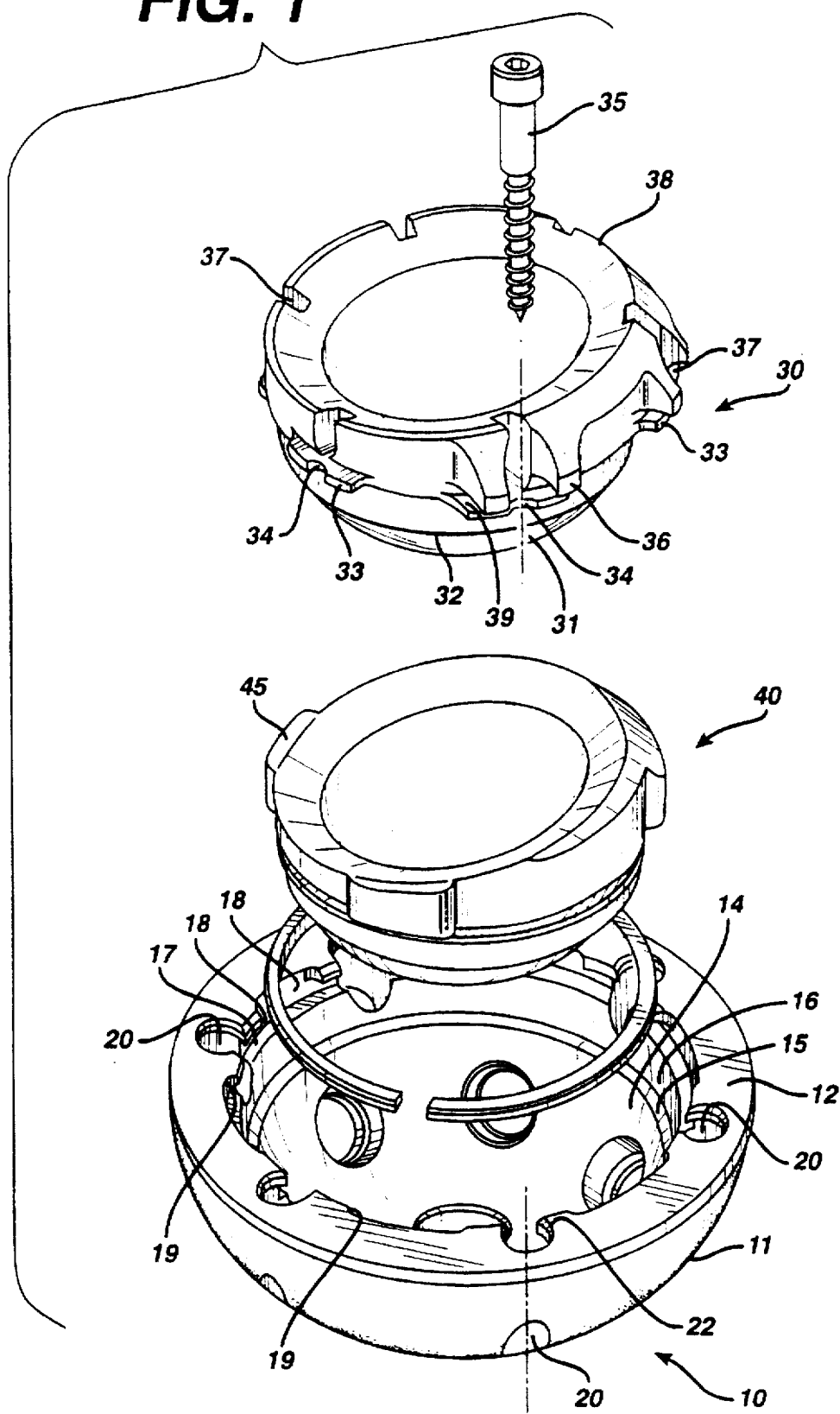
FIG. 1 illustrates a perspective view of the system of the present invention including the insert-then-orient liner, the snap-in liner and the acetabular shell of the present invention.

Referring now to FIGS. 1 through 4 an acetabular shell 10 is illustrated. The shell 10 comprises an outer spherical surface 11 having a porous coating formed thereon, an outer rim 12 having a plurality of pin openings 20 extending through the rim 12 and the outer spherical surface 11 of the shell 10. The shell 10 further comprises an inner spherical surface 14 including a ridge 15 extending around the circumference of the shell 10 forming a first groove 16. A second ridge 17 forms a second groove 18 extending around the inner circumference of the inner spherical surface 14 adjacent the rim 12. The groove has a greater outer circumference than the circumference defined by the ridge 17. Tab protrusions 22 extend from the rim 12 adjacent the pin holes 20 over the groove 18 defining indentations 19 in the rim 12.

Insert-then-orient liner 30 is illustrated in FIG. 1 comprising an outer spherical surface 31 generally matching the inner spherical surface 14 of the shell 10. The liner 30 also comprises a ridge 32 arranged to sit on top of the ridge 15 of the shell 10. The ridge 32 extends around the circumference of the liner 30. The liner 30 further comprises lower lugs 33 adjacent the ridge 32, 34 having an indentation for permitting a pin or screw 35 to pass through the openings 20 of the outer shell 10 and engage a lower lug 33 of the liner 30. The liner 30 also comprises upper lugs 36 also having openings 37 for engaging a pin 35 inserted through openings 20 of the shell 10. The upper lugs 36 and lower lugs 33 are spaced from each other to define a second groove 39 therebetween. The liner further comprises an angularly asymmetric upper rim portion 38 extending around the outer circumference of the top of the liner 30.

The outer spherical surface of the insert may be inserted in the opening of the shell 10 by aligning the upper and lower lugs 36, 33 with the indentations 19 in the rim 12 of the shell 10. When the liner 30 is inserted, the ridge 32 of the liner 30 sits on top of the ridge 15 of the shell 10 the lower lugs 33 fit within the groove 18 of the shell 10 while the upper lugs 36 fit just above the rim 12 of the shell 10. The liner 30 is then rotated so that the openings 34, 37 in the lugs 33, 36 align with the openings 20 in the shell 10 to form the pin holes for receiving pin 35. The tab protrusions 22 of the shell 10 extend into the second groove 39 between the upper and lower lugs 36, 33 in the liner 30. The tab protrusions 22 in the shell 10 engage the upper lugs 36 to prevent the liner 33 from coming out of the shell 10. The liner 30 is then rotated within the shell 10 to a desired angular orientation and in a position where the openings 34, 37, 20 are aligned. A pin or screw 35 is then inserted through the hole formed by the openings 34, 37, 20. The pin 35 engages with the shell 10 and the top of the liner 30 to prevent rotation of the liner 30 with respect to the shell 10.

The liner 30 is removable from the shell 10 at any time until a pin 35 is placed in position, by rotating the liner 30 into the initial position where the lugs 33, 37 are aligned with the indentations 22 in the rim 12 of the shell 10.

Figure 2:
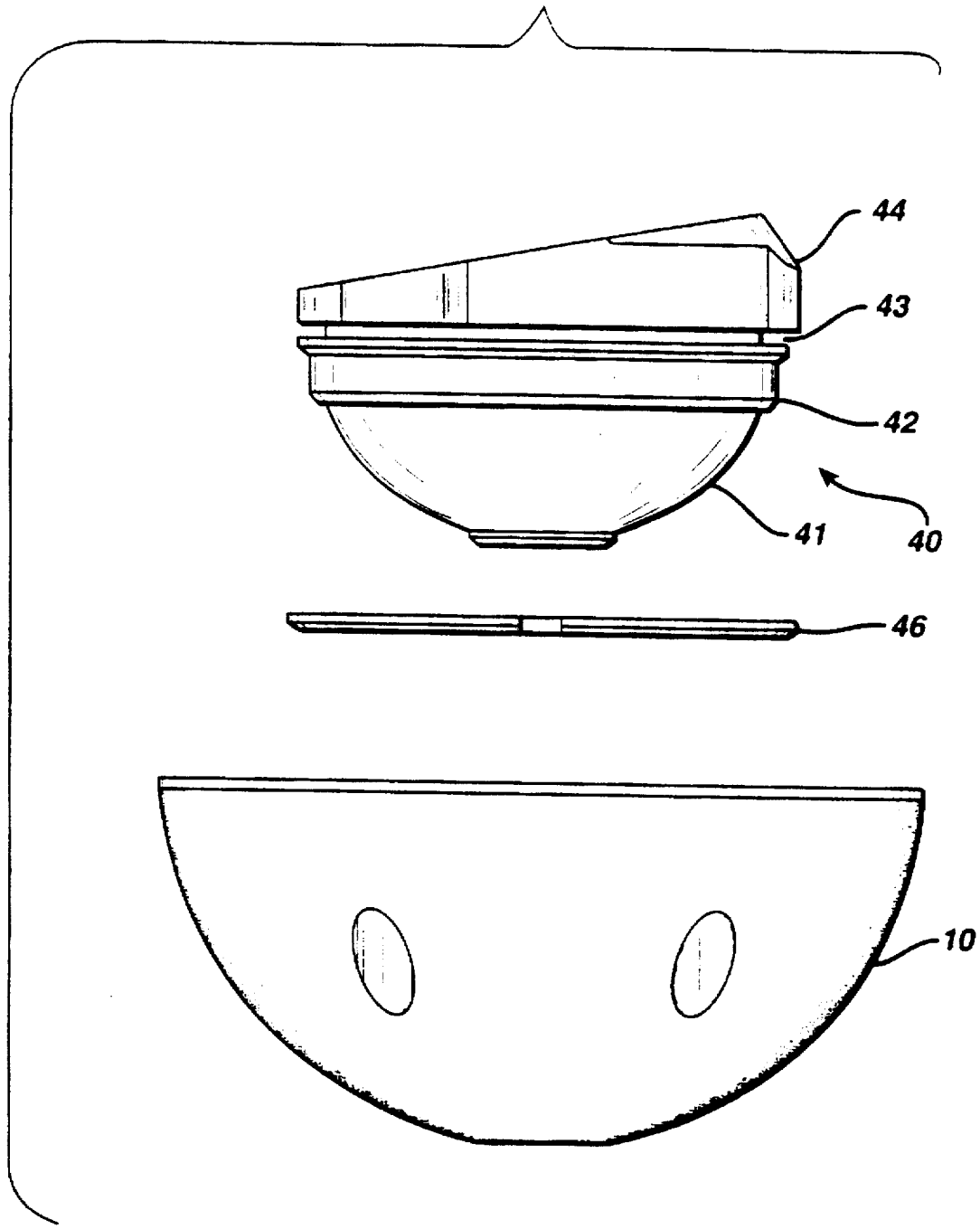
FIG. 2 illustrates a side view of the snap-in liner and acetabular shell of the present invention.
Figure 3:
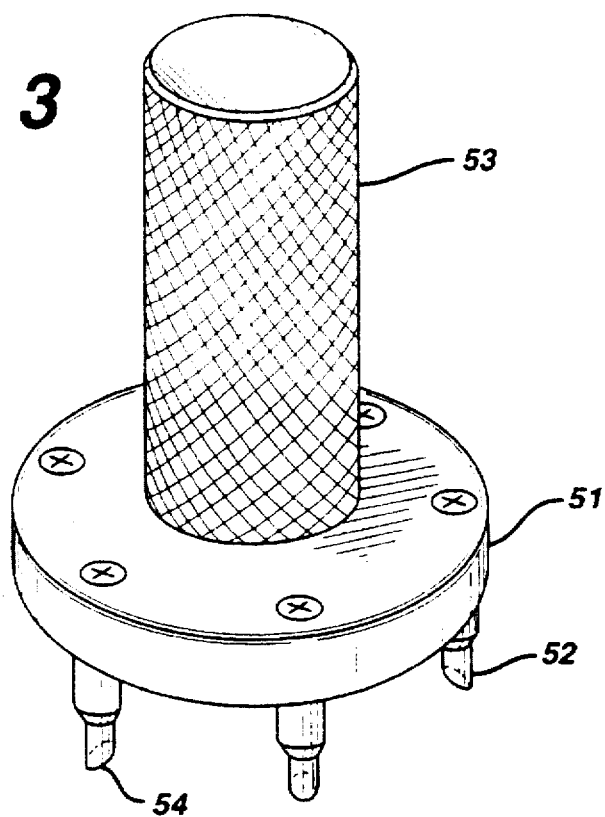
FIG. 3 illustrates an instrument for removing the liner of FIG. 2.
Figure 4:
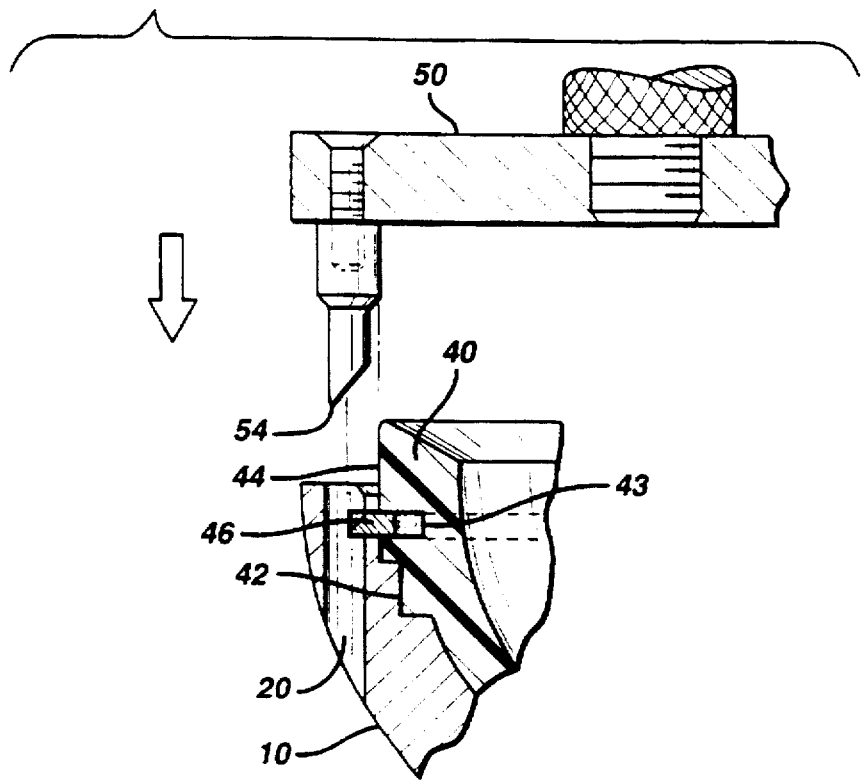
FIG. 4 illustrates a cross-sectional view of the instrument of FIG. 3 in use with the acetabular cup of FIG. 2.

A snap-in liner 40 is illustrated in FIGS. 1, 2 and 4. This liner 40 comprises an outer spherical surface 41, a ridge 42, and a groove 43 extending around the outer circumference of the liner 40. Adjacent the groove 43 at the outer edge of the liner 40, is an asymmetric ring portion 44 including lugs 45 extending in predetermined spaced positions around the outer circumference of the ring 44. The insert 40 further comprises a separate resilient metal ring 46 sized to fit within the groove 43 and extending radially from the groove 43.

In use, the metal ring 46 is placed within the groove 43 of the liner 40. The liner 40 is placed within the inner spherical surface 14 of the shell 10 with the lugs 45 resting on top of the rim 12 of the shell 10. The liner 40 may then be rotated to orient the angular position of the asymmetric ring portion 44 into a proper or ideal location. The lugs 45 are then moved into a position to over the nearest indentation 22 in the rim 12 and the liner 40 is pressed into the shell 10 in a position in which the lugs 45 extend into the first groove 16 of the shell 10 and prevent removal of the liner 40 from the shell 10. The metal ring 46 of the insert resiliently expands to extend partially within the groove 18 of the shell 10 while remaining partially within the groove 43 to secure the liner 40 with the shell 10. The lugs 45 prevent rotation of the liner 40 with respect to the shell 40 by engaging protrusions 19 on the shell 10.

When the liner 40 is inserted into the shell 10, the ring 46 is visible within the openings of the shell 10. An instrument 50 such as that illustrated in FIG. 3 may be used to remove the liner 40 from the shell 10. The instrument 50 comprises a cylindrical body 51 with a handle 53 and prongs 52 extending from the body 51. The prongs 52 correspond to opening 20 in the shell 10. In use, the prongs 52 are inserted into the openings 20 in the shell 10. The prongs 52 include angled tips 54, that compress the metal ring 46 into the groove 43 and out of the groove 18, freeing the ring 46 from engagement with the shell 10. The liner 40 may then be removed from the shell 10 without significant damage to the shell 10 or the liner 40. If desired, the liner 40 may be repositioned with respect to the shell 10 and reinserted.

In use a surgeon inserts an acetabular cup into position in the patient and selects which of the liners to use. The selected liner is then oriented and located in the ideal position within the metal cup as described above. In the event the insert-then-rotate-liner is used, the pins may be inserted into the pin holes to lock or secure the orientation of the insert with respect to the metal cup.

Although this invention is described with reference to specific embodiments, various modifications may be made without departing from the scope of the inventions claimed herein.

We claim:

1. A prosthetic acetabular cup system for surgical implantation comprising:

an outer shell comprising: a cavity for receiving a liner, the liner forming a bearing for receiving a ball portion of a ball and socket joint, said cavity defining a plane through which the liner enters the cavity, and said cavity comprising an axis perpendicular to said plane;

a plurality of acetabular cup liners from which a liner may be selected to be placed within said outer shell for implanting into a patient;

each of said plurality of liners comprising a cavity and a circumferential rim about said cavity extending out of said plane when said liner is inserted into said shell, each of said plurality of liners having a plurality of selectable orientations, said plurality of selectable orientations being angularly displaced from one another about said axis and relative to said plane;

said plurality of acetabular liners comprising:

a first liner and a second liner;

wherein said system comprises a first fixation device for fixing the first liner to the shell in one of said plurality of orientations and a second fixation device different from said first fixation device for fixing the second liner to the shell in one of said plurality of orientations;

wherein said first liner is arranged so that an orientation is first selected from said plurality of orientations before said liner is inserted into said shell and said first fixation device fixes said first liner in a said orientation within said shell when said first liner is inserted into said shell; and wherein said second liner is arranged so that an orientation is selected after said liner is inserted into said shell and said second fixation device fixes said second liner in a said orientation after said liner is inserted into said shell and then said orientation is selected.

2. The system of claim 1 wherein said first liner comprises an outer surface having a groove therein;

wherein said first fixation device comprises a resilient ring within said groove biased towards a position radially extending from said groove.

3. The system of claim 2 wherein said shell comprises a groove for receiving said ring.

4. The system of claim 3 wherein said first liner and said shell form at least one opening; and wherein said ring extends into said at least one opening when said first liner is inserted into said shell.

5. The system of claim 4 further comprising a liner remover for removing said first liner from said shell after said first liner is inserted into said shell, said liner remover comprising:

a handle coupled to at least one prong for placement within said at least one opening to compress said ring within said groove of said liner to release said ring from said groove of said shell.

6. The system of claim 1 wherein said second fixation device comprises a pin; and wherein said second liner and said shell form an opening for receiving said fixation pin when said second liner is placed in a said orientation.

7. The system of claim 6 wherein said second fixation device further comprises a plurality of lugs located on an outer surface of said liner, said opening adjacent said lugs; wherein said pin impinges on said lugs when inserted into said opening to impede rotational movement of said liner with respect to said shell.

* * * * *